(12) United States Patent
Kong et al.

(10) Patent No.: US 6,896,854 B2
(45) Date of Patent: May 24, 2005

(54) NONTHERMAL PLASMA SYSTEMS AND METHODS FOR NATURAL GAS AND HEAVY HYDROCARBON CO-CONVERSION

(75) Inventors: Peter C. Kong, Idaho Falls, ID (US); Lee O. Nelson, Idaho Falls, ID (US); Brent A. Detering, Idaho Falls, ID (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 371 days.

(21) Appl. No.: 10/059,669

(22) Filed: Jan. 29, 2002

(65) Prior Publication Data

US 2003/0141182 A1 Jul. 31, 2003
US 2005/0056533 A9 Jul. 31, 2003

Related U.S. Application Data

(63) Continuation-in-part of application No. 10/057,543, filed on Jan. 23, 2002.

(51) Int. Cl.[7] .................................................. B01J 19/08
(52) U.S. Cl. ............................... 422/186.3; 422/186.04
(58) Field of Search ......................... 422/186.3, 186.04

(56) References Cited

U.S. PATENT DOCUMENTS

| | | | |
|---|---|---|---|
| 3,616,381 A | * 10/1971 | Krenzke et al. | ............ 204/168 |
| 5,427,747 A | 6/1995 | Kong et al. | ................. 422/186 |
| 6,087,405 A | 7/2000 | Plecha et al. | ................ 518/715 |
| 6,117,814 A | 9/2000 | Plecha et al. | ................ 502/325 |
| 6,124,367 A | 9/2000 | Plecha et al. | ................ 518/715 |
| 2003/0136661 A1 | * 7/2003 | Kong et al. | ................... 204/168 |

OTHER PUBLICATIONS

Chang et al., "EHD Surface Waves of Diesel Oil Thin Films Generated by Wire–Plate Barrier Discharges," 1997 IEEE Annual Report—Conference On Electrical Insulation And Dielectric Phenomena, Minneapolis, Oct. 19–22, 1997.
Park, et al., "Generation of atmospheric pressure plasma with a dual–chamber discharge," Applied Physics Letters, vol. 77, No. 14, Oct. 2, 2000.
Urashima et al., "The Effect of Gravity Direction on the EHD Surface Waves of Dielectric Oil Thin Films Generated by Wire–Plate Barrier Discharges," IEEE 1998.

* cited by examiner

Primary Examiner—Steven Versteeg
(74) Attorney, Agent, or Firm—Trask Britt, P.C.

(57) ABSTRACT

A reactor for reactive co-conversion of heavy hydrocarbons and hydrocarbon gases and includes a dielectric barrier discharge plasma cell having a pair of electrodes separated by a dielectric material and passageway therebetween. An inlet is provided for feeding heavy hydrocarbons and other reactive materials to the passageway of the discharge plasma cell, and an outlet is provided for discharging reaction products from the reactor. A packed bed catalyst may optionally be used in the reactor to increase efficiency of conversion. The reactor can be modified to allow use of a variety of light sources for providing ultraviolet light within the discharge plasma cell. Methods for upgrading heavy hydrocarbons are also disclosed.

26 Claims, 11 Drawing Sheets

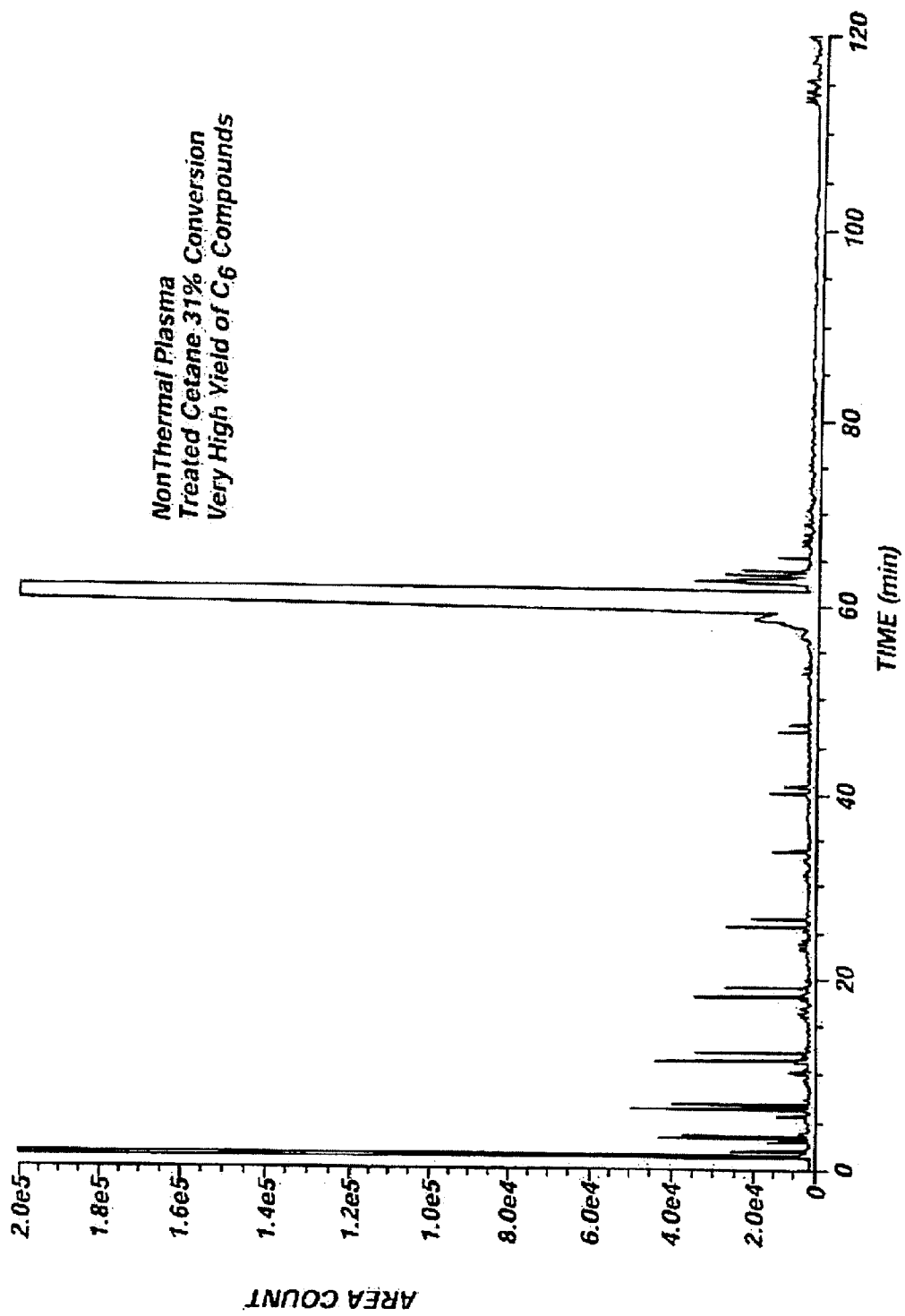

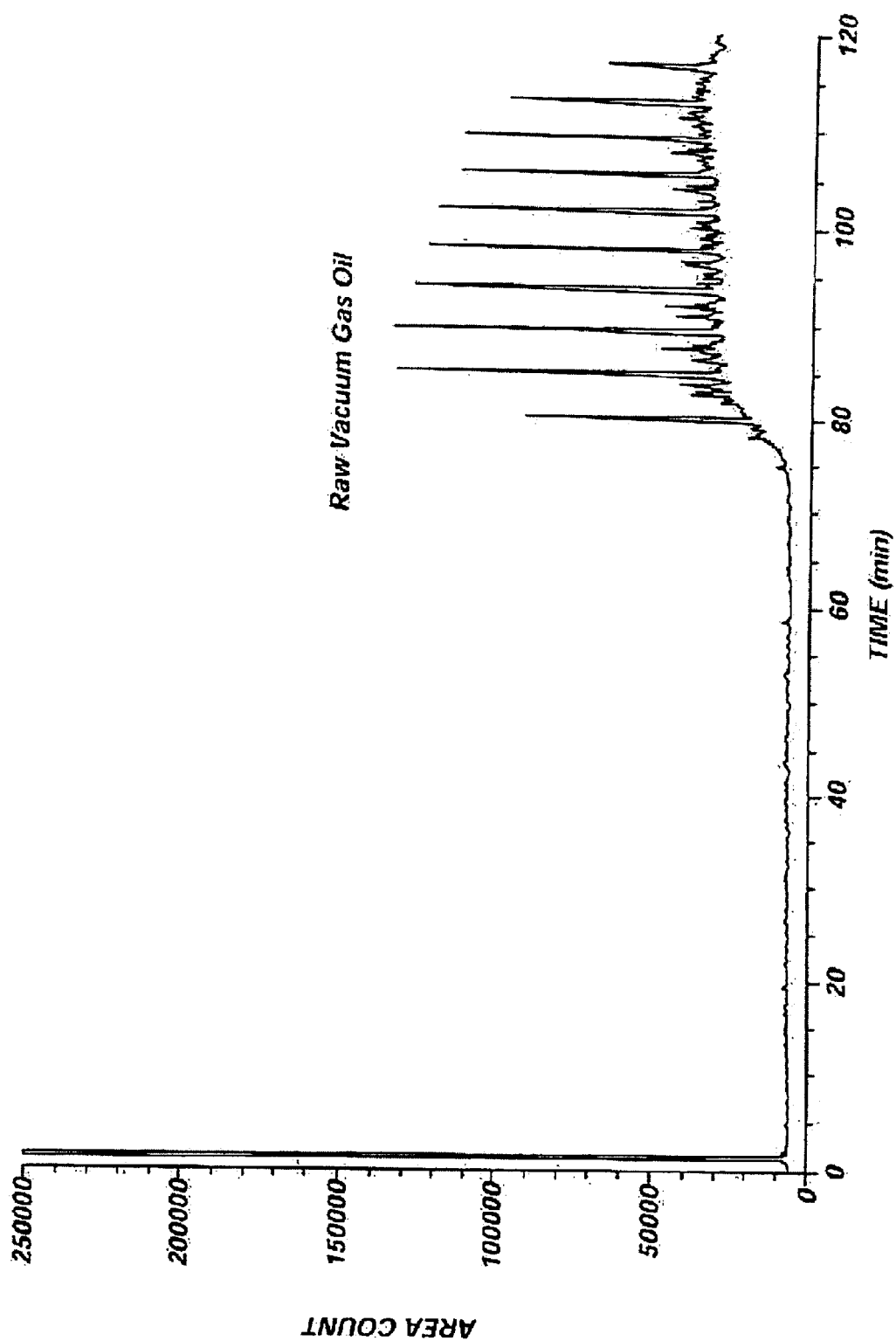

NONTHERMAL PLASMA SYSTEMS AND METHODS FOR NATURAL GAS AND HEAVY HYDROCARBON CO-CONVERSION

CROSS-REFERENCE TO RELATED APPLICATIONS

This application is a continuation-in-part of, and claims benefit under 35 U.S.C. §120 of, U.S. application Ser. No. 10/057,543, filed Jan. 23, 2002, and entitled APPARATUS AND METHODS FOR DIRECT CONVERSION OF GASEOUS HYDROCARBONS TO LIQUIDS, pending.

STATEMENT OF GOVERNMENT INTEREST

The U.S. Government has certain rights in this invention pursuant to Contract No. DE-AC07-99ID13727, and Contract No. DE-AC07-05ID14517 between the U.S. Department of Energy and Battelle Energy Alliance, LLC.

BACKGROUND OF THE INVENTION

1. Field of the Invention

The present invention relates to techniques for reactively converting hydrocarbons. More particularly, the invention relates to systems and methods for reactive co-conversion of heavy hydrocarbon materials and hydrocarbon gases to lighter hydrocarbon materials.

2. Background Technology

Heavy hydrocarbon materials, such as heavy oil, include any petroleum/crude oil that has a low API (American Petroleum Institute) gravity of less than 20 API degrees or a high specific density of more than about 0.9 g/ml. Heavy oil is quite viscous, does not flow well and has a high carbon to hydrogen ratio along with a high amount of carbon residues due to coking process, asphaltenes, sulfur, nitrogen, and heavy metals. The importance of heavy oil is increasing as more supplies of light oil start to decrease and run out. Most of the world's remaining oil resources and reserves primarily contain heavy oil.

Generally, oil refineries are designed for handling lighter crude oils, which typically have a density of about 0.8 g/ml or less. Because heavy oils have a higher density, a high sulfur content, and are highly viscous (sometimes over 1000 times more viscous than light crude oil), they are less than ideal for conventional oil refineries. Therefore, in order to capitalize on heavy oils as a source for transportation fuel, present processes found in the art seek to upgrade heavy oils into a practical intermediate to sell and transport to refineries.

One of the goals of upgrading is to make the heavy oil capable of being transported by pipeline without adding a solvent. Currently, solvents are usually required which require an additional solvent-recovery process. The ultimate goal of upgrading is to make an economically valuable synthetic crude oil. However, this requires large, expensive plants, much like refineries. Further, current processes requires multiple steps.

For example, one process of upgrading heavy oils uses a solvent to dilute the heavy oil, which is then distilled. Large molecules that will not distill out are thermally cracked at over 400° C. to produce lighter hydrocarbons. Since the resulting product is rich in nitrogen and sulfur, a second thermal cracking step is required to reduce sulfur content. Thermal cracking requires hydrogen gas to stabilize the process. The hydrogen suppresses coke formation and helps remove sulfur.

The current state of the art for upgrading heavy oil can be divided into two general approaches: 1) hydrogen addition, and 2) carbon rejection. Hydrogen addition processes are often desirable because of high liquid yield. However, these types of processes are expensive, requiring high temperature and pressure equipment as well as a hydrogen source. Carbon rejection plants and processes are also desirable because they are less expensive to construct and operate. However, carbon rejection processes produce large quantities of very low-grade materials, which are not always readily marketable or disposable, and with heavy oils, have high yield losses.

Methane remains another vastly unused resource. Methane is an abundant hydrocarbon fuel and chemical feed stock, and is expected to remain so for quite some time. Yet, because of capital and technological barriers, methane has remained an under-utilized resource throughout the world.

Thus, it would be desirable to provide improved methods for upgrading heavy oils that avoid or overcome the difficulties and problems of prior techniques.

SUMMARY OF THE INVENTION

The present invention contemplates both systems and methods for reactive co-conversion of heavy hydrocarbons such as heavy crude oil and hydrocarbon gases such as natural gas to lighter hydrocarbon materials such as synthetic light crude oil. Such upgrading of heavy crude oils is accomplished by a dielectric barrier discharge plasma process that adds carbon and hydrogen simultaneously to heavy oil during upgrade in a single step. The upgraded product formed includes transportation fuels and enriched synthetic light crude oil, which is readily acceptable to existing refineries.

A chemical reactor is utilized in the systems and methods of the invention for reactive co-conversion of heavy hydrocarbons and hydrocarbon gases such as natural gas. The reactor includes a dielectric barrier discharge plasma cell having a pair of electrodes separated by a dielectric material and passageway therebetween. An inlet is provided for feeding heavy hydrocarbons and other reactive materials to the passageway of the discharge plasma cell, and an outlet is provided for discharging reaction products from the reactor. A packed bed catalyst may optionally be used in the reactor to increase efficiency of the co-conversion.

In an alternative embodiment, a chemical reactor includes a dielectric barrier discharge plasma cell which is adapted to be used with an ultraviolet (UV) light source. The light source can be positioned within an electrode of the discharge plasma cell. The electrode is constructed to allow transmission of UV light into the reactor. A packed bed catalyst can optionally be used in this reactor along with the light source to increase efficiency of the co-conversion.

The present invention provides for the exploitation of significantly underutilized low market value heavy oil and natural gas resources to meet current energy needs. The present invention provides systems and methods for the conversion of these low market value raw materials to high market value commodities.

These and other features and advantages of the present invention will become more fully apparent from the following description and appended claims, or may be learned by the practice of the invention as set forth hereinafter.

BRIEF DESCRIPTION OF THE DRAWINGS

In order to illustrate the manner in which the above recited and other advantages of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which:

FIGS. 5A–5C are gas chromatograms depicting area count (Area count is the relative amount or percentage of composition of a component in a mixture of products) vs. time for a first example of a reactive co-conversion of methane and cetane; and FIGS. 6A–6B are gas chromatograms depicting area count vs. time for a second example of a reactive co-conversion of methane and vacuum gas oil.

DETAILED DESCRIPTION OF THE INVENTION

The present invention is directed to systems and methods for reactive co-conversion of a wide range of hydrocarbon materials including but not limited to heavy hydrocarbons such as heavy crude oil and hydrocarbon gases such as natural gas to lighter hydrocarbon materials such as synthetic light crude oil. Such upgrading of heavy crude oils is accomplished by a dielectric barrier discharge plasma process that adds carbon and hydrogen simultaneously to heavy oil during upgrade in a single step. The process of the present invention essentially acts as a single step refinery process. Heavy oils and hydrocarbon gases go in to a reactor, and lighter synthetic crude oils and transportation fuels come out. The only step that remains in the process is to separate the various products. Methane or other hydrocarbon gases can be used in the process to more efficiently convert heavy oils to lighter hydrocarbons. The upgraded products of transportation fuels and enriched synthetic light crude oil are readily acceptable to existing refineries, or may not even require further refining.

The present invention raises the market value of the heavy oils by reducing nitrogen, sulfur, and heavy metals in the raw heavy oil feed stock, thereby upgrading heavy oils to useful products. The present invention also benefits refinery operations by reducing operation and maintenance costs, as well as environmental liability costs. In addition, the methods of the invention provide for upgrading heavy oils at low economic cost and high production yields.

Figure 1:
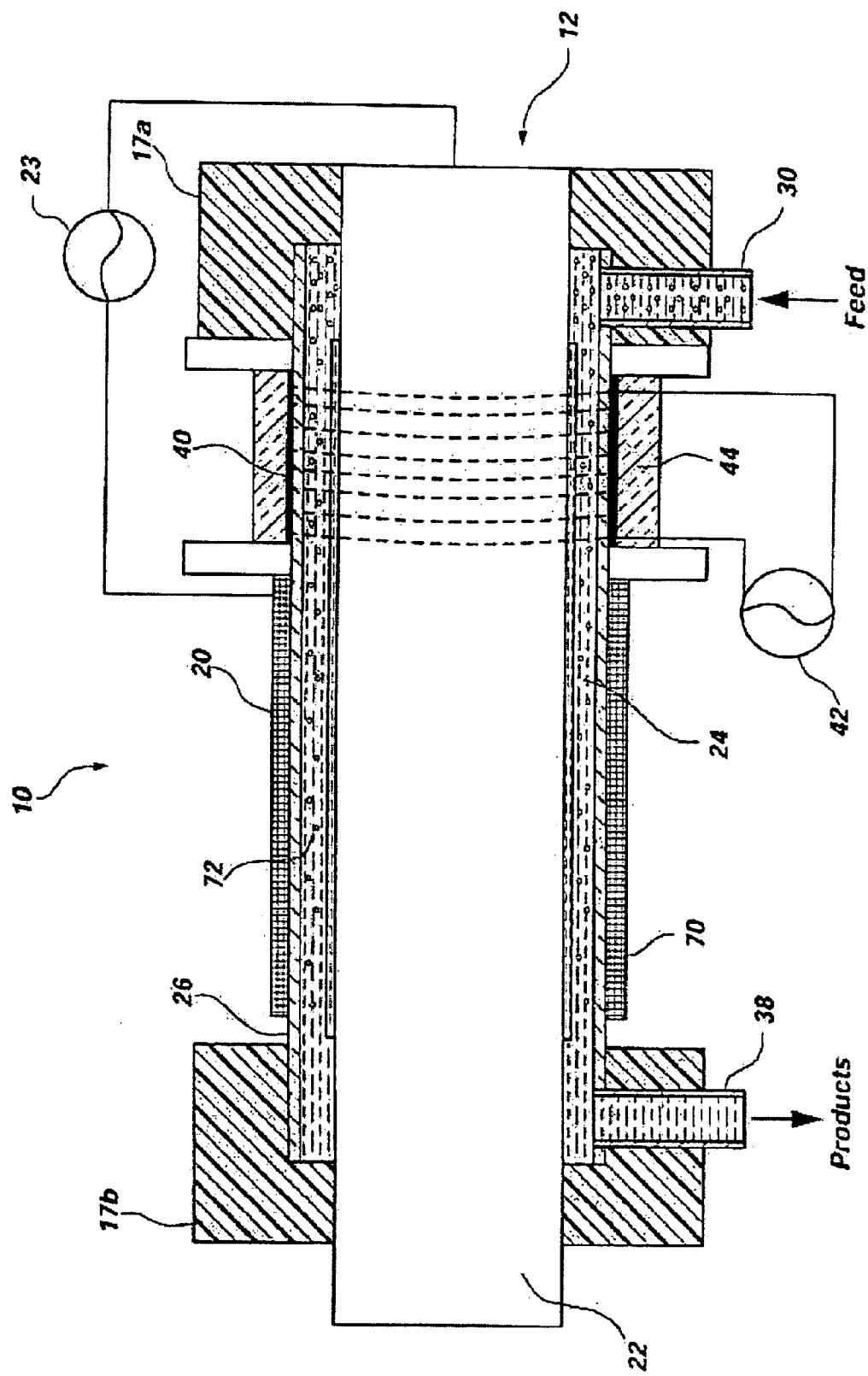
FIG. 1 is a schematic cross-sectional view of an apparatus for reactive co-conversion of heavy hydrocarbons and hydrocarbon gases such as natural gas and in accordance with one embodiment of the invention.

Referring to the drawings, wherein like structures are provided with like reference designations, FIG. 1 depicts a chemical reactor 10 used for upgrading of heavy hydrocarbons (e.g., cetane) according to one embodiment of the invention. The reactor 10 generally comprises a longitudinally elongated dielectric barrier discharge plasma cell 12, preferably having opposing end caps 17a and 17b, which can be made of a Teflon material, polytetrafluoroethylene (PTFE) material, or other suitable material to withstand the reaction conditions.

The discharge plasma cell 12 comprises an outer electrode 20 and an inner electrode 22 which are operatively connected to a high voltage AC/DC power supply 23 that is used to initiate and sustain the plasma. The outer electrode 20 can take the form of an elongated metal cylindrical screen shell which is partially surrounding and supported by a support tube 26. Suitable materials of construction for outer electrode 20 are stainless steel, and the like. The inner electrode 22 can take the form of an elongated rod member, which can be either solid or hollow. The inner electrode 22 is disposed concentrically internal of outer electrode 20 and within support tube 26. Suitable materials of construction for inner electrode 22 are stainless steel, titanium, nickel, gold, and the like. In an alternative embodiment, inner electrode 22 can be constructed of a catalytic material or can have a catalyst material coating thereon, which is discussed more fully hereafter. The electrode 22 is centrally positioned within support tube 26 to define a central axis of plasma cell 12.

The support tube 26 provides a barrier layer and is formed of a dielectric material. The support tube 26 can be composed of a ceramic oxide material such as quartz, as well as zirconia, alumina, glass, and the like. A passageway 24 in the shape of an elongated annulus is defined between support tube 26 and electrode 22. A hydrocarbon inlet 30 extends from the exterior of end cap 17a to annular passageway 24. A product outlet 38 extends from passageway 24 to the exterior of endcap 17B.

An electric heater 40 such as a furnace is provided in discharge plasma cell 12 for maintaining the reactants in the reactor at a desired temperature condition. A power supply 42 is operatively connected to heater 40, and an insulation layer 44 surrounds heater 40 to keep the heat inside the reactor.

As mentioned previously, electrode 22 can be constructed of a catalytic material or can have a catalyst material coating thereon, which enhances the formation of desired fuel products. Some metals are known to be catalytic to hydrocracking and hydrotreating of a hydrocarbon feed stream. Examples of these metals are cobalt (Co), nickel (Ni), platinum (Pt), rhenium (Re), molybdenum (Mo), tungsten (W), and palladium (Pd). These metals can be manufactured as single metal or bimetal fine powders supported on porous hollow cylinders and spheres of alumina, silica, or zeolite. These supported catalysts can be used for natural gas and heavy hydrocarbon liquid co-conversion to light hydrocarbon liquids. Other examples of hydrocracking catalysts are NiMo, CoMo, and CoW. Examples of hydrotreating catalysts are Ni, Co, Pt, and Re.

There are various configurations which can be employed for a catalytic electrode. In one embodiment, electrode 22 can comprise a non-catalytic base metal (e.g., stainless steel) with single metal or bimetal catalysts deposited on the electrode surface as discrete nanoparticles for either hydrocracking or hydrotreating of the feed materials. Alternatively, two different metal catalysts could be zone deposited on the electrode surface as discrete nanoparticles for successive catalytic hydrocracking and hydrotreating of the feed materials.

In another embodiment, electrode 22 can comprises a catalytic base metal with a second catalytic metal deposited on the electrode surface as discrete nanoparticles. For example, the electrode can be fabricated from Co or Ni, and the second metal, such as Mo, W or Pt, is deposited on the electrode surface as discrete nanoparticles.

In yet another embodiment, electrode 22 can comprise a catalytic base metal with two other catalytic metals being zone deposited on the electrode surface as discrete nanoparticles. This allows successive catalytic hydrocracking and hydrotreating of the feed materials because the different metals will produce different reactions. For example, the base metal can be fabricated from Co or Ni, while one metal, for example Mo, is deposited in a first zone proximal to the feed source, and a second metal, for example W, is deposited in a second zone on the electrode distal from the feed source.

One skilled in the art will recognize that a variety of configurations may be suitably employed to perform the functions set forth herein for a catalytic electrode. The single metal and bimetal catalytic design for configuring electrode 22 are only illustrative and should not be construed as limiting the scope of the present invention.

Figure 2:
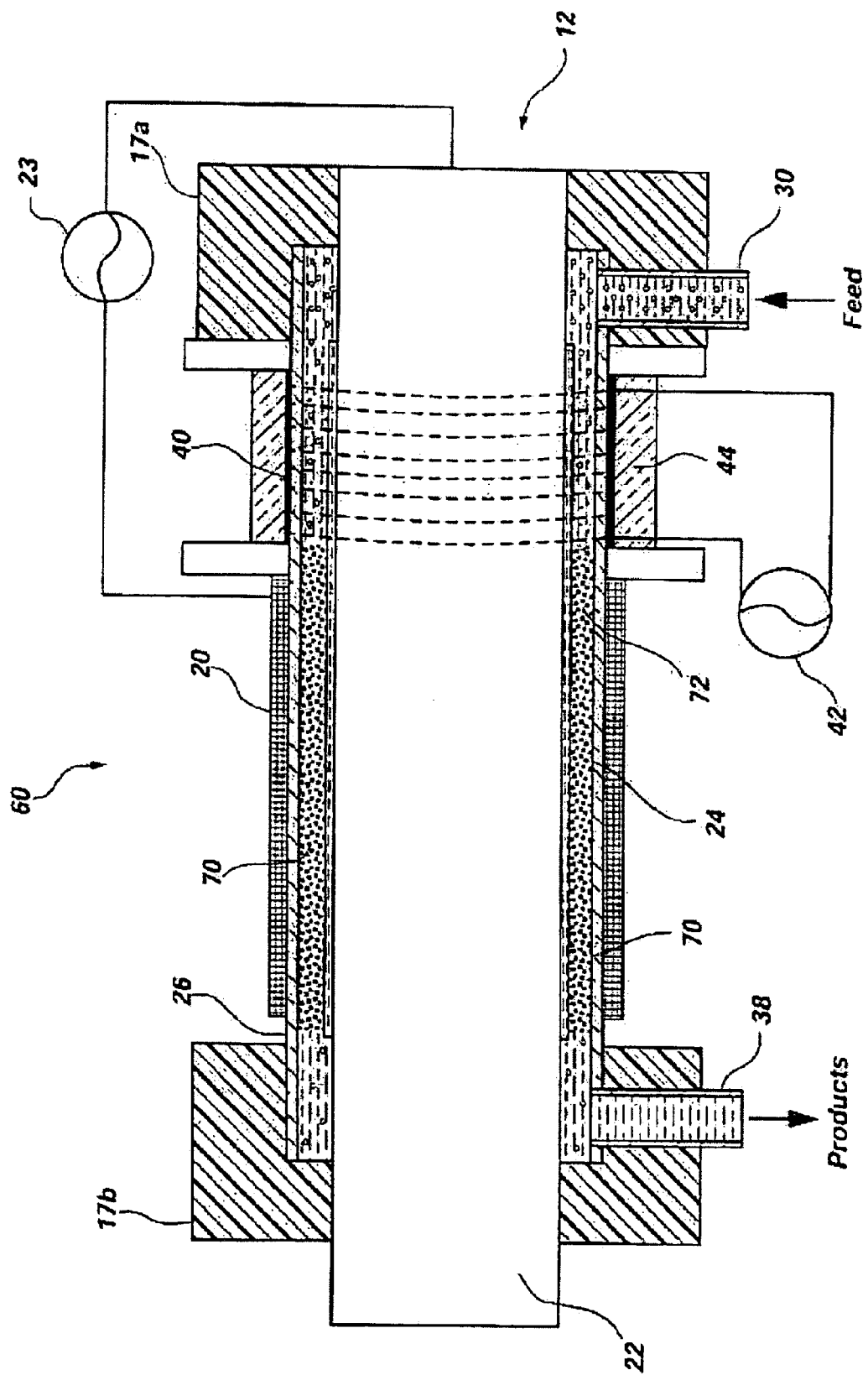
FIG. 2 is a schematic cross-sectional view of an apparatus for reactive co-conversion of heavy hydrocarbons and hydrocarbon gases such as natural gas in accordance with another embodiment of the invention.

FIG. 2 depicts a chemical reactor 60 used for upgrading of heavy hydrocarbons such as heavy oils according to an alternative embodiment of the invention. The reactor 60 includes components similar to those discussed above with respect to reactor 10. Accordingly, reactor 60 generally comprises a dielectric barrier discharge plasma cell 12, which is preferably self-supported within opposing end caps 17a and 17b.

The discharge plasma cell 12 comprises an outer electrode 20 and an inner electrode 22 which are operatively connected to a power supply 23. The outer electrode 20 partially surrounds and is supported by a support tube 26. The inner electrode 22 is disposed concentrically internal of outer electrode 20 and within support tube 26. A passageway 24 is defined between support tube 26 and electrode 22. A hydrocarbon inlet feed 30 extends from the exterior of housing end cap 17a to passageway 24. A product outlet 38 extends from passageway 24 to the exterior of endcap 17B. A power supply 42 is operatively connected to a heater 40, and an insulation layer 44 surrounds heater 40.

In addition, a packed bed catalyst 70 is disposed in reactor 60 within passageway 24, as shown in FIG. 2. The packed bed catalyst 70 can be used to control the types of products that reactor 60 yields. Suitable materials for the packed bed catalyst include those appropriate for the catalytic electrode 22 discussed previously. Generally, any hydrocracking catalysts, hydrotreating or hydrogenating catalysts, or a combination of these catalysts can be used for heavy oil and natural gas conversion. Under the influence of non-thermal plasma, the catalysts may have increased activity.

In one embodiment, the packed bed catalyst 70 may comprise a single catalytic zone configuration. This configuration includes a single catalyst component bed for either hydrocracking or hydrotreating of the feed material. In an alternative embodiment, the packed bed catalyst 70 may comprise a double zone configuration. This configuration includes alternating the catalyst components in passageway 24 for successive hydrocracking and hydrotreating of the feed material. It should be noted that a variety of configurations may be suitably employed to perform the functions set forth herein for the packed bed catalyst. The single zone and double zone configurations for packed bed catalyst 70 are only illustrative and should not be construed as limiting the scope of the invention. In addition, the packed bed catalyst may be used in conjunction with a catalytic electrode as described previously.

During operation of chemical reactor 10 or reactor 60, a heavy hydrocarbon feed, such as a heavy oil and a hydrocarbon gas such as natural gas, is directed through inlet 30 into a plasma zone 72 created in passageway 24. The hydrocarbon feed is subjected to a dielectric barrier discharge generated between electrodes 20 and 22 in plasma zone 72. Such a dielectric barrier discharge produces a non-equilibrium or "cold" plasma in which the electron temperature is typically very high (i.e., about $10^4$ K.), while the gas temperature remains at ambient (i.e., less than about 373 K.). Specifically, when a high voltage (i.e., about 1000 or greater AC/DC volts) is applied between electrodes 20 and 22, the dielectric barrier formed by dielectric support tube 26 effectively breaks down, enabling multiple discharges to be maintained between dielectric support tube 26 and central electrode 22. The discharges are in the form of micro-arcs which induce dissociation and ionization of gases. The dissociation of gases in this type of discharge generates a high concentration of free radicals, in the plasma state, which are reactive at high rates. The discharges are effective to generate radicals and cause partial hydrogen abstraction from the hydrocarbon molecules, such as the difficult to cleave C—H bond in methane. A voltage range of 3–6 kV can be used to sustain the plasma discharge. This voltage range is not limiting, and can be varied depending on the capability of the power supply used. A uniform and stable blue glow from the plasma is observed when the power supply is turned on.

The operating conditions of a dielectric barrier discharge cell are discussed more fully in U.S. Pat. No. 5,427,747 to Kong et al. (hereinafter the "Kong patent"), the disclosure of which is incorporated herein by reference.

Free radicals formed within passageway 24 are caused to flow inwardly toward outlet 38. Ambient temperature operation of the discharge plasma cell 12 should prevent solid carbon formation during the discharge because complete hydrogen abstraction from the hydrocarbons is not encouraged. Accordingly, there is a corresponding enhancement in the efficiency of liquid fuel formation. The reaction temperature is generally maintained from about 300° C. to about 400° C. However, the temperature is not limited to this range and can be higher or lower depending on the reaction requirements. The ratio of the reactants can change over a wide range based on specific process needs. The light hydrocarbon liquid products form a liquid film along electrode 22 in passageway 24, and the liquid products are discharged through product outlet 38. The various products exiting the reactor can then be separated by conventional techniques as desired.

Numerous possible reactions involved in the dielectric barrier discharge are discussed in the Kong patent. Preferably, methane can be added to the feed to assist in formation of fuel-type liquids. The purpose for having methane in the feed stream is that when the methane reacts with the larger hydrocarbons, it will add more side branches. The more branched a hydrocarbon chain is, the higher the octane number becomes for the liquid fuel product. One skilled in the art will recognize that other lighter hydrocarbons may be added to the feed stream to produce higher octane fuels. For example, any of the $C_1$ to $C_4$ hydrocarbons may be used. Using different hydrocarbon gases should produce different products. Furthermore, a range of heavy hydrocarbons can be fed with a range of lighter hydrocarbons to produce a range of fuel-type products.

In the method of the invention, both methane and heavy hydrocarbons are activated in the dielectric barrier discharge plasma and these reactants are cracked to smaller molecular fragments. In the process, excess hydrogen is also produced. The hydrogen produced in the process then hydrogenates the hydrocarbon fragments to form light hydrocarbon compositions. The light hydrocarbons produced can be significantly high in gasoline and diesel compositions, or other fuel products.

Figure 3A:
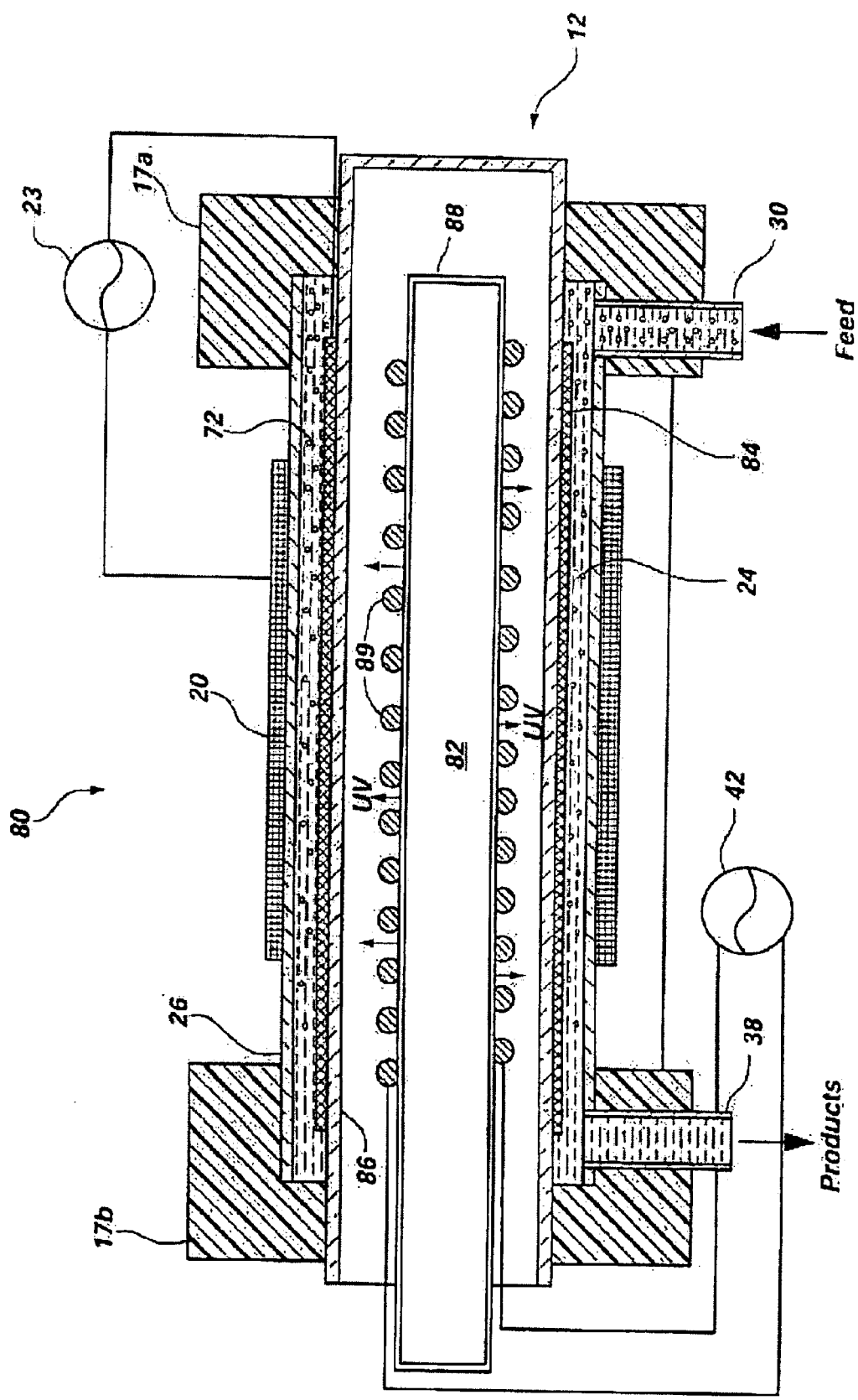
FIG. 3A is a schematic cross-sectional view of an apparatus for reactive co-conversion of heavy hydrocarbons and hydrocarbon gases such as natural gas in accordance with an alternative embodiment of the invention.

In accordance with another embodiment of the invention, FIG. 3A illustrates a chemical reactor 80 that can be used for upgrading of heavy hydrocarbons according to a further embodiment of the invention. The reactor 80 includes components similar to those discussed above with respect to reactor 10, except that reactor 80 is adapted to be used with an ultraviolet (UV) light source 82 to provide UV light-enhanced conversion of heavy hydrocarbons. Thus, reactor 80 generally comprises a dielectric barrier discharge plasma cell 12 is preferably self-supported within a pair of endcaps 17a and 17b.

The discharge plasma cell 12 comprises an outer electrode 20 and an inner electrode 84 which are operatively connected to a power supply 23. The outer electrode 20 partially surrounds and is supported by a support tube 26. The inner electrode 84 is disposed internally of outer electrode 20 and within support tube 26. A passageway 24 is defined between support tube 26 and electrode 84. A hydrocarbon gas inlet feed 30 extends from the exterior of the housing to annular passageway 24. A product outlet 38 extends from passageway 24 to the exterior of endcap 17B.

As shown in FIG. 3A, UV light source 82 can be positioned within electrode 84. The electrode 84 is constructed such that UV light can pass into passageway 24. For example, electrode 84 can be constructed of a metallic screen shell. The electrode 84 can be constructed of the same materials as described for electrode 22 previously. A UV light housing structure 86 may be used to support electrode 84 as shown in FIG. 3A. The UV light housing structure 86 is preferably constructed of a transparent material, such as glass or quartz, such that UV light is permitted to pass through structure 86, past electrode 84 and into passageway 24. The UV light source 82 can also be provided with wall structure 88. One skilled in the art will recognize that housing structures 86 and wall structure 88 may be substituted with other configurations as needed. For example, other configurations may include electrode 84 without a supporting housing structure, while the UV light source may have a housing structure, or vice-versa.

The UV light source also supports a plurality of electric heating elements 89 for maintaining the reactants at a desired temperature condition. A power supply 42 is operatively connected to heater elements 89.

Figure 3B:
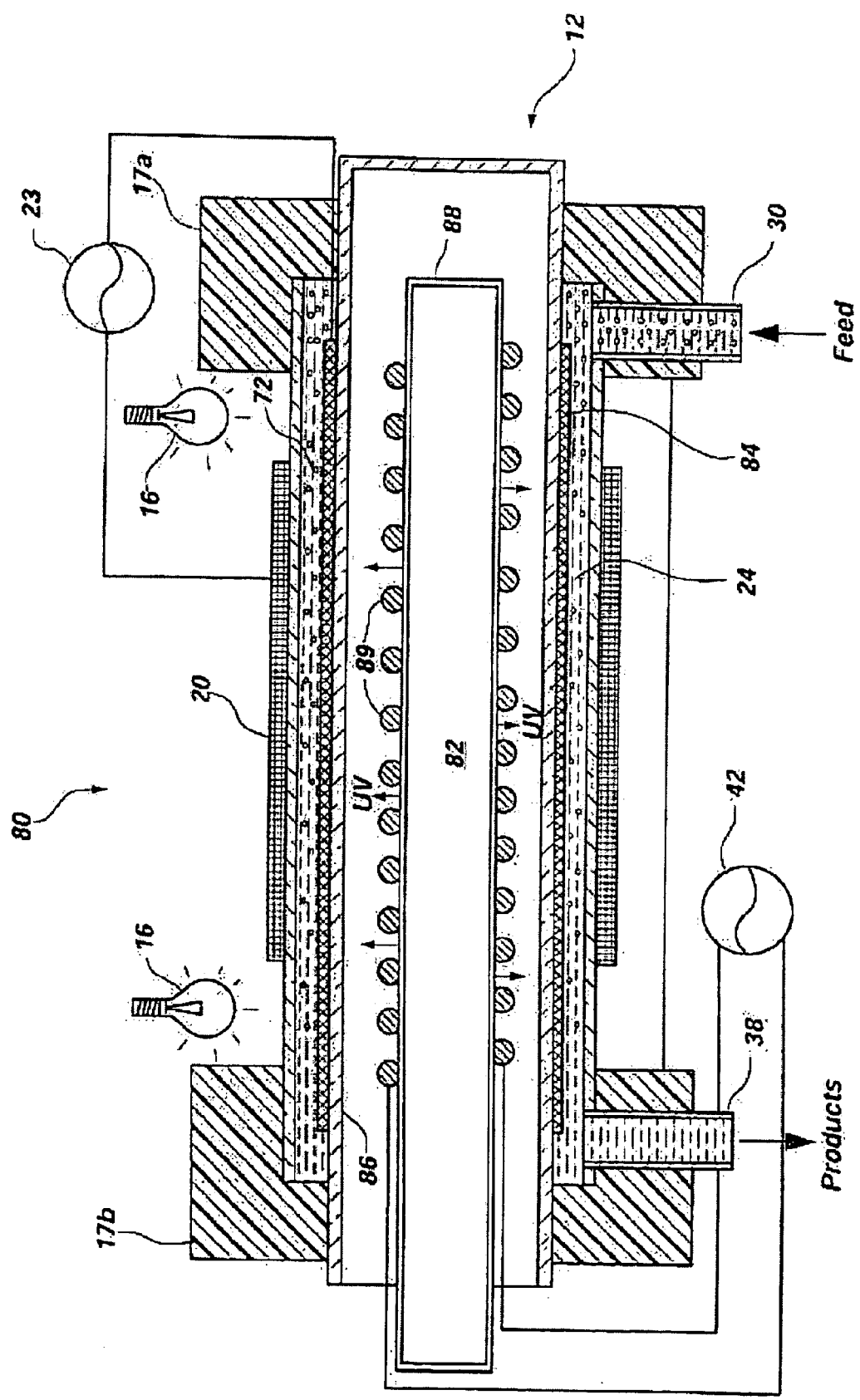
FIG. 3B is a schematic cross-sectional view of an apparatus for reactive co-conversion of heavy hydrocarbons and hydrocarbon gases such as natural gas in accordance with a further alternative embodiment of the invention.

Alternatively and as illustrated in FIG. 3B, one or more external UV light sources 16 may be placed external alternative reactor 80' when at least a portion of the structure 86 is UV transparent, allowing UV light to be transmitted into the reactor from outside. Such a configuration can be used in lieu of or in combination with UV light source 82 being disposed within electrode 84.

Figure 4A:
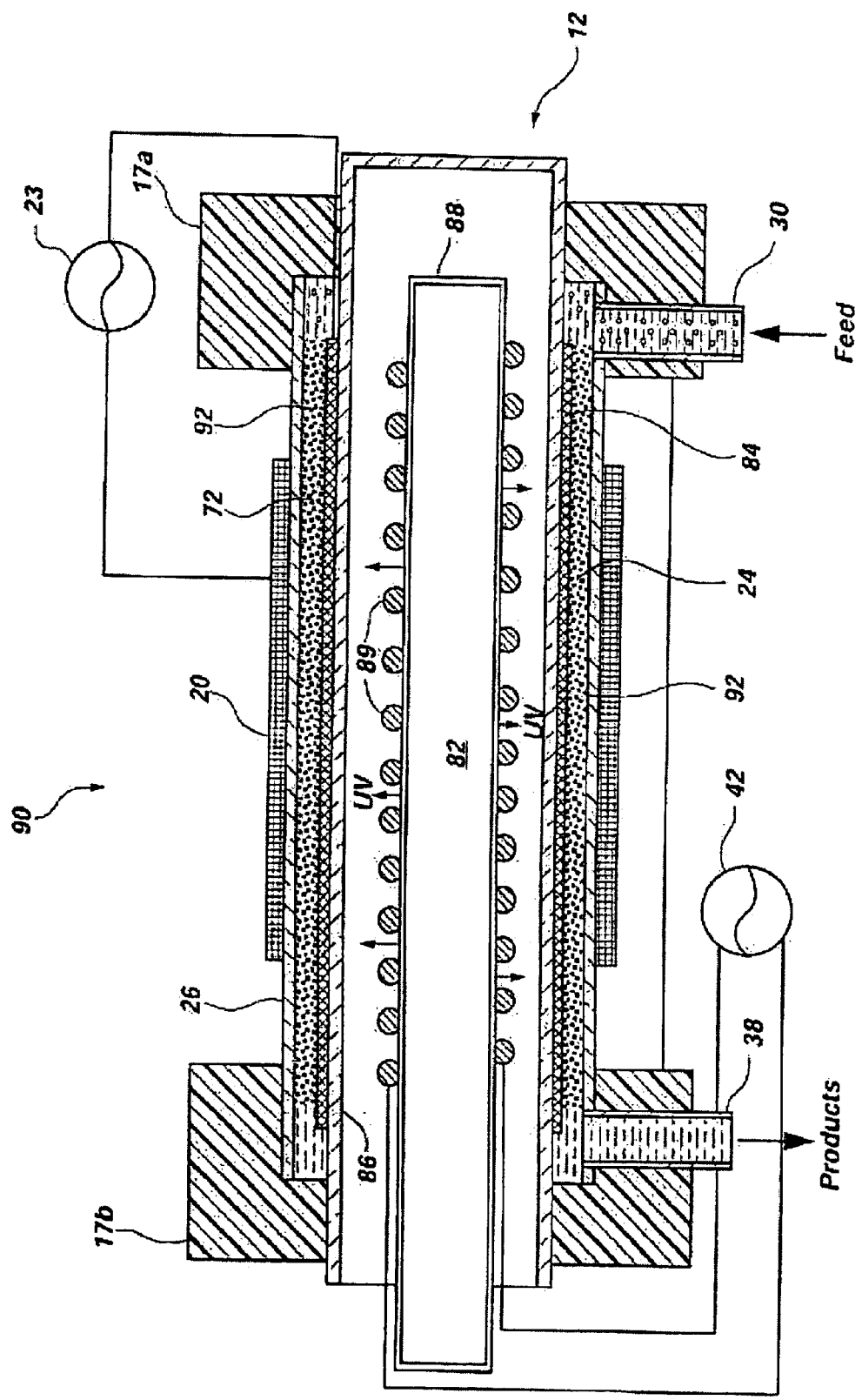
FIG. 4A is a schematic cross-sectional view of an apparatus for reactive co-conversion of heavy hydrocarbons and hydrocarbon gases such as natural gas in accordance with a yet further alternative embodiment of the invention.

FIG. 4A illustrates a chemical reactor 90 that can be used for upgrading of heavy hydrocarbons according to an alternative embodiment of the invention. The reactor 90 includes components similar to those discussed above with respect to reactor 80, being adapted to be used with a UV light source 82. Thus, reactor 90 generally comprises a dielectric barrier discharge plasma cell 12 which includes essentially the same components as discussed above for reactor 80, including an outer electrode 20 and an inner electrode 84, with a UV light source 82 positioned within electrode 84. The outer electrode 20 partially surrounds and is supported by a support tube 26. A passageway 24 is defined between support tube 26 and electrode 84. A hydrocarbon gas inlet feed 30 extends from the exterior of the housing to passageway 24, and a product outlet 38 extends from passageway 24. A housing structure 86 may be used to support electrode 84. The UV light source 82 can also be provided with an optional UV light source housing structure 88. The UV light source and/or structure 88 supports a plurality of electric heating elements 89 operatively connected to a power supply 42.

In addition, a packed bed catalyst 92 is disposed in reactor 90 within a passageway 24 as shown in FIG. 4A. The packed bed catalyst 92 can be used to control the types of products that reactor 90 yields. Suitable materials for packed bed catalyst 92 include those discussed previously for packed bed catalyst 70 of reactor 60. Thus, any hydrocracking catalysts, hydrogenating catalysts, or a combination of these catalysts can be used for heavy oil and natural gas co-conversion. The packed bed catalyst 92 may comprise a single catalytic zone configuration or a double zone configuration, as described previously for packed bed catalyst 70. In addition, the packed bed catalyst 92 may be used in conjunction with a catalytic electrode 84.

During operation of chemical reactor 80 or reactor 90, light from UV light source 82 transmits though electrode 84 into plasma zone 72 of passageway 24. The UV light enhances the energy level of the plasma in passageway 24, which is typically under atmospheric pressure, thereby increasing the reactivity of the plasma for materials processing. Simultaneously, the UV light also excites the molecular bonds of the reactants and more completely cracks the reactants to smaller molecular fragments. This higher energy state plasma and the UV light activate methane more efficiently and generate higher concentrations of hydrocarbon and hydrogen radicals. During the reaction process, excess hydrogen is produced and hydrogenates the hydrocarbon fragments to form light hydrocarbon compositions such as synthetic crude oils. The light hydrocarbons are significantly high in gasoline and diesel compositions.

Because of higher energy and reactivity available from the UV-plasma coupled systems, the reactions therein may be sustainable below about 300° C. However, the temperature is not limited to this value and can assume a higher or lower value depending on the reaction requirements.

Figure 4B:
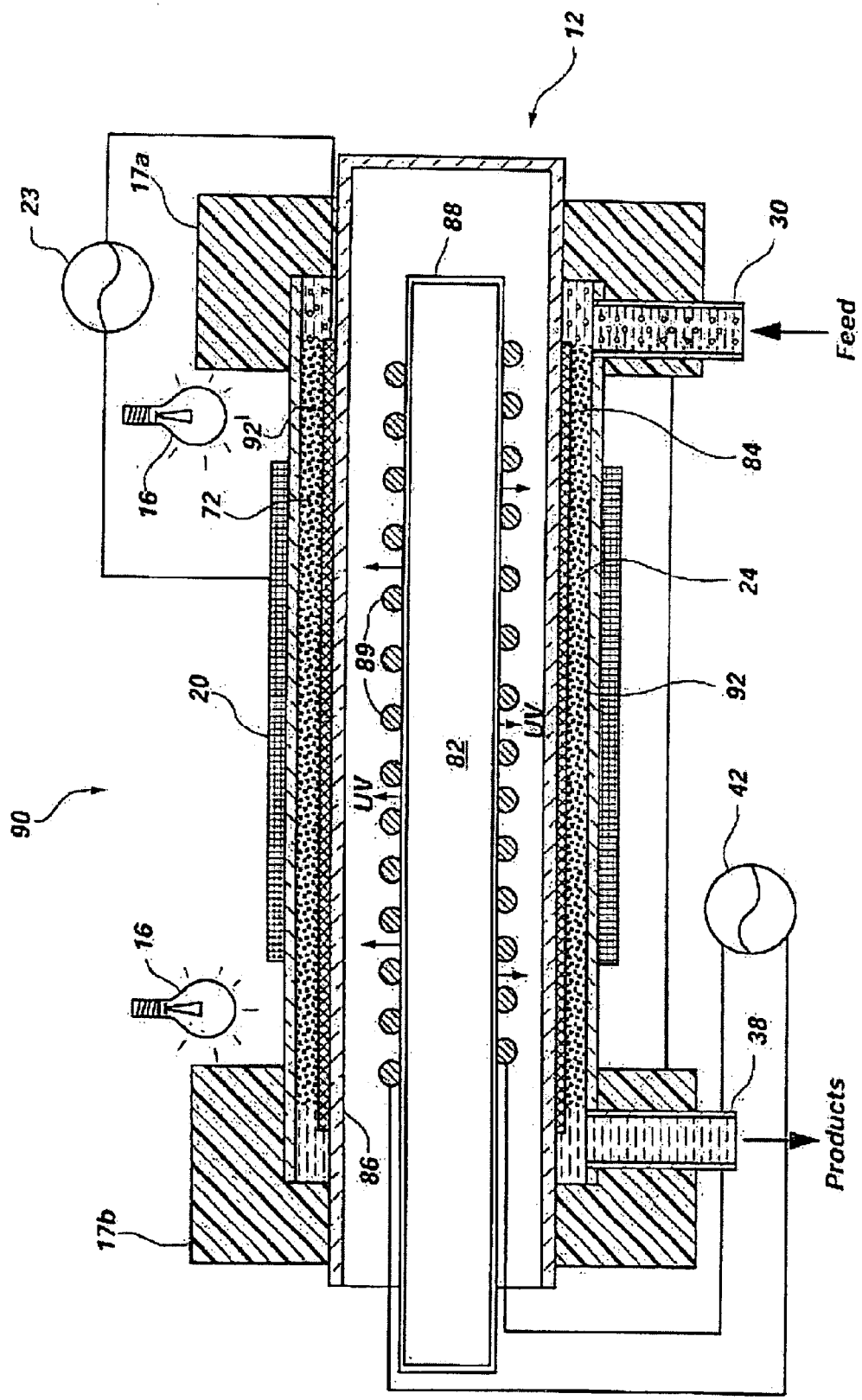
FIG. 4B is a schematic cross-sectional view of an apparatus for reactive co-conversion of heavy hydrocarbons and hydrocarbon gases such as natural gas in accordance with a still yet further alternative embodiment of the invention.

In FIG. 4B, an alternative reactor 90' is illustrated having at least one external UV light source 16 to provide a UV light source in lieu of or in combination with UV light source 82 to enhance, or elevate, the energy state of the plasma. Otherwise the operation of reactor 90' is as described with respect to reactor 90 illustrated in FIG. 4A.

The systems and methods of the present invention provide many benefits and advantages. The present invention advantageously exploits the significantly under-utilized low market value heavy oil and natural gas resources to meet current energy needs. The methods of the invention convert these low market value raw materials to high market value commodities. The invention will benefit oil producers and processors by: (1) producing significantly more usable natural resources; (2) producing high market value synthetic feed stock from low value raw materials; (3) reducing environmental pollutant precursors in the feed stock; (4) reducing facility operation and maintenance costs; and (5) reducing long term environmental liability risks.

The following examples are given to illustrate the present invention, and are not intended to limit the scope of the invention.

EXAMPLE 1

Figure 5A:
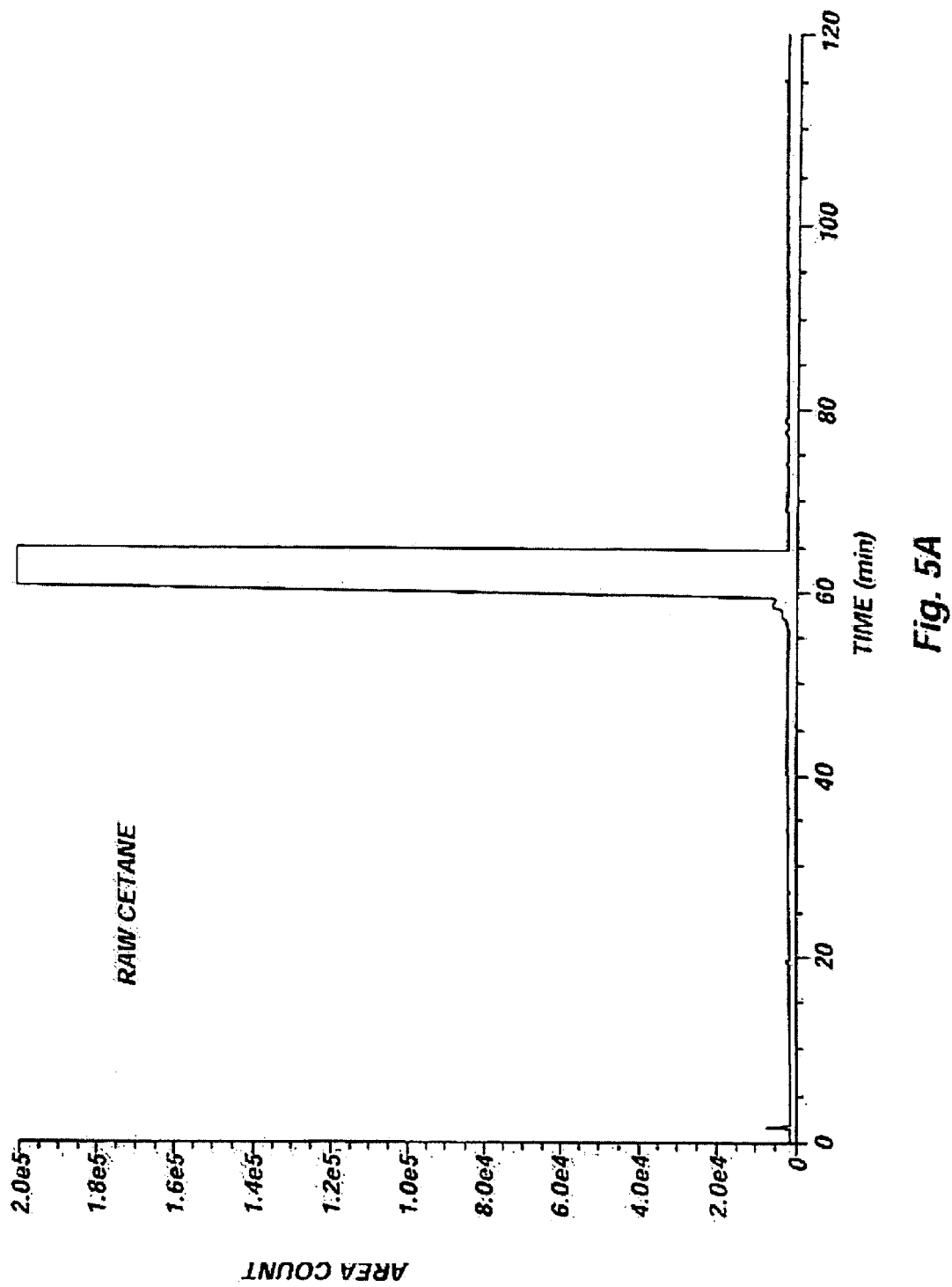
Figure 5B:
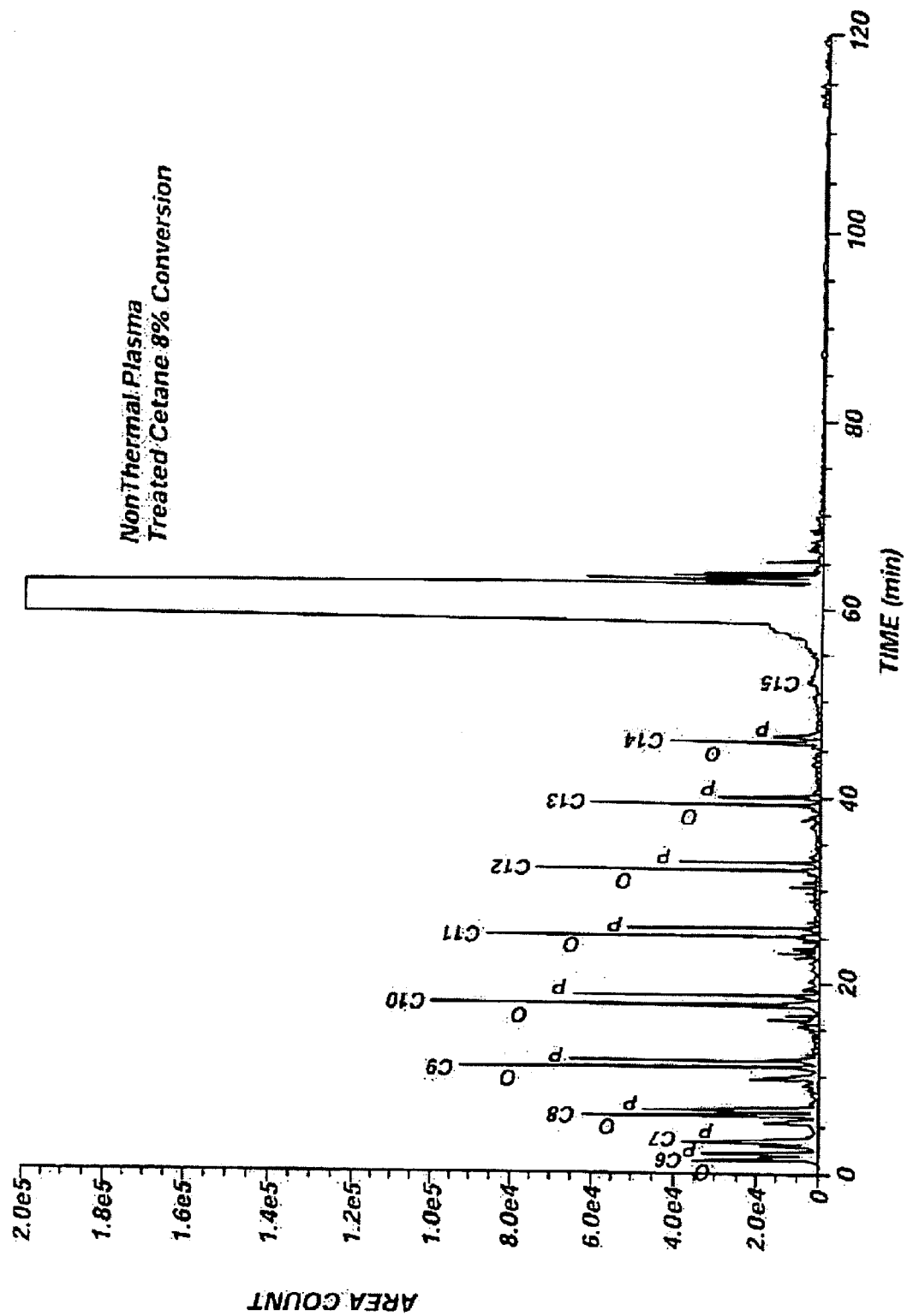

Example 1 demonstrates the reactive co-conversion of methane and cetane (hexadecane, $H_{16}C_{34}$) in a nonthermal plasma reactor in accordance with the present invention. FIG. 5A is the gas chromatogram (GC) profile of a cetane feed. The applied voltage of the plamsa reactor is between 6–7 kV. The feed rate for cetane was about 0.01 cc/minute and the feed rate for methane was between about 100–250 cc/minute. FIG. 5B depicts the GC profile of the reaction product without a catalyst pack bed. FIG. 5C depicts the GC profile of the reaction product with a nickel catalyst pack bed. The reaction with the nickel catalyst pack bed in a nonthermal plasma in accordance with the present invention demonstrates the ability of the present invention to provide a substantially higher conversion of cetane in a single pass to produce gasoline like products.

EXAMPLE 2

Figure 6B:
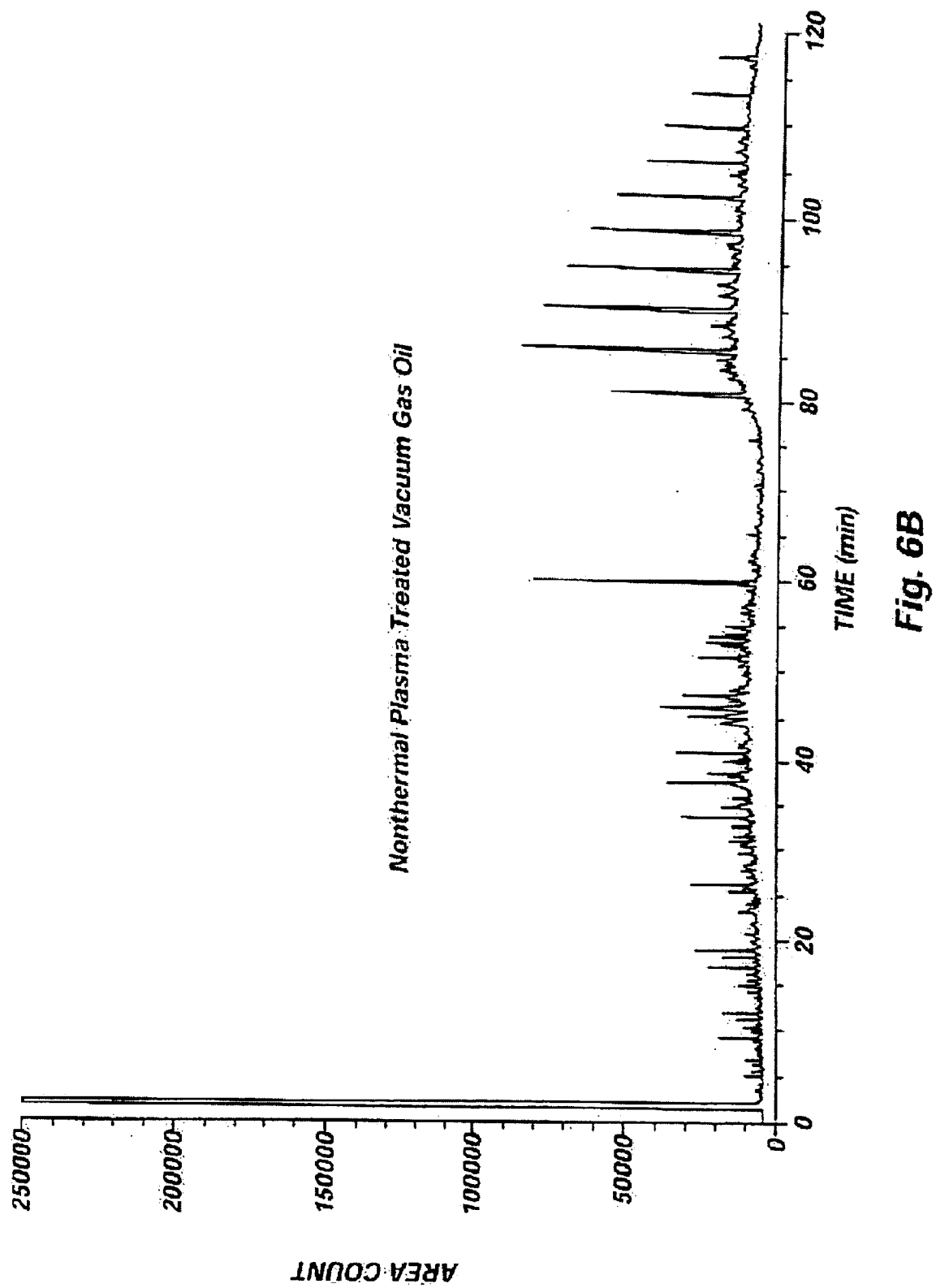

Example 2 demonstrates the reactive co-conversion of methane and vacuum gas oil (VGO) in a nonthermal plasma reactor in accordance with the present invention. The VGO has a carbon number significantly larger than $C_{20}$. FIG. 6A is the GC profile of the raw VGO feed. The applied voltage of the plasma reactor is between 6–7 kV. The feed rate for VGO was about 0.01 cc/minute and the feed rate for the methane was about 100–250 cc/min. FIG. 6B depicts the GC profile of the reaction product without a catalyst pack bed. The reaction shows significant conversion of VGO in a single pass to gasoline and light diesel like products.

Generally speaking, if at least one hydrocarbon gas such as methane is not present in the reactive co-conversion process in accordance with the present invention, such as in the above examples, there will be some conversion of the heavy hydrocarbon feed materials due to cracking of heavy hydrocarbons thereby forming hydrocarbon gases from the feed materials during the reaction process. However, for efficiency and for producing the greatest amount of conversion of heavy hydrocarbons into lighter hydrocarbons, it is preferred and most advantageous to include at least one hydrocarbon gas such as methane or another C1 through C4 hydrocarbon within the reactor to maximize the efficiency and amount of heavy hydrocarbons being co-converted with the at least one hydrocarbon gas into lighter hydrocarbons.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

We claim:

1. An apparatus for reactive co-conversion of hydrocarbons, comprising:

a dielectric barrier discharge plasma cell comprising an outer electrode and an inner electrode with a dielectric material and a passageway therebetween, the inner electrode comprising a catalyst material;

an inlet for feeding hydrocarbons to the passageway of the discharge plasma cell; and an outlet for discharging reaction products from the passageway.

2. The apparatus of claim 1, wherein the inner electrode is constructed of a catalyst material.

3. The apparatus of claim 1, wherein the inner electrode has a catalyst material coating thereon.

4. The apparatus of claim 1, wherein the catalyst material comprises a hydrocracking catalyst or a hydrotreating catalyst.

5. The apparatus of claim 1, wherein the inner electrode comprises a non-catalytic base metal, and a bimetal catalyst overlying the base metal.

6. The apparatus of claim 1, wherein the inner electrode comprises a non-catalytic base metal, and two different bimetal catalysts overlying the base metal for successive catalytic hydrocracking and catalytic hydrotreating of feed hydrocarbons.

7. The apparatus of claim 1, wherein the inner electrode comprises a first catalytic base metal, and a second catalytic metal overlying the base metal.

8. The apparatus of claim 1, wherein the inner electrode comprises a catalytic base metal, and two different catalytic metals overlying the base metal for successive catalytic hydrocracking and catalytic hydrotreating of feed hydrocarbons.

9. The apparatus of claim 1, wherein the inner electrode comprises one or more materials selected from the group consisting of cobalt, nickel, platinum, rhenium, molybdenum, tungsten, palladium, and combinations thereof.

10. An apparatus for reactive co-conversion of hydrocarbons, comprising:

a dielectric barrier discharge plasma cell comprising an outer electrode and an inner electrode with a dielectric material and a passageway therebetween;

an inlet for feeding hydrocarbons to the passageway of the discharge plasma cell;

an outlet for discharging reaction products from the passageway; and a packed bed catalyst in the passageway of the discharge plasma cell, wherein the packed bed catalyst comprises a material selected from the group consisting of a hyrocracking catalyst, a hydrotreating catalyst, and combinations thereof.

11. The apparatus of claim 10, wherein the inner electrode comprises a catalyst material.

12. The apparatus of claim 10, wherein the inner electrode is constructed of a catalyst material.

13. The apparatus of claim 10, wherein the inner electrode has a catalyst material coating thereon.

14. The apparatus of claim 10, wherein the packed bed catalyst comprises at least two zones, including at least one zone having a hydrocracking catalyst material disposed therein and at least one other zone having a hydrotreating catalyst material disposed therein.

15. The apparatus of claim 10, wherein the packed bed catalyst comprises one or more materials selected from the group consisting of cobalt, nickel, platinum, rhenium, molybdenum, tungsten, palladium, and combinations thereof.

16. An apparatus for reactive co-conversion of hydrocarbons, comprising:

a dielectric barrier discharge plasma cell comprising an outer electrode and an inner electrode with a dielectric material and a passageway therebetween;

an inlet for feeding hydrocarbons to the passageway of the discharge plasma cell;

an outlet for discharging reaction products from the passageway; and at least one light source for directing ultraviolet light into the discharge plasma cell.

17. The apparatus of claim 16, wherein the inner electrode comprises a catalyst material.

18. The apparatus of claim 16, wherein the inner electrode is constructed of a catalyst material.

19. The apparatus of claim 16, wherein the inner electrode has a catalyst material coating thereon.

20. The apparatus of claim 16, wherein the at least one light source is positioned within the inner electrode.

21. The apparatus of claim 20, wherein the inner electrode is constructed of a metallic screen shell.

22. The apparatus of claim 20, wherein the inner electrode is supported by a structure having at least a portion thereof which is transparent.

23. The apparatus of claim 16, wherein the at least one light source is positioned outside the inner electrode.

24. The apparatus of claim 16, further comprising a packed bed catalyst in the passageway of the discharge plasma cell.

25. The apparatus of claim 24, wherein the packed bed catalyst comprises a material selected from the group consisting of a hydrocracking catalyst, a hydrogenating catalyst, and combinations thereof.

26. The apparatus of claim 24, wherein the packed bed catalyst comprises one or more materials selected from the group consisting of cobalt, nickel, platinum, rhenium, molybdenum, tungsten, palladium, and combinations thereof.

* * * * *